US00PP10943P

United States Patent [19]

Fuess

[11] Patent Number: Plant 10,943

[45] Date of Patent: Jun. 8, 1999

[54] CHRYSANTHEMUM PLANT NAMED 'EMPIRE NOSTALGIA'

[76] Inventor: Janet S. Fuess, 22 Country Club Dr., New York Mills, N.Y. 13417

[21] Appl. No.: 08/968,246

[22] Filed: Nov. 12, 1997

[51] Int. Cl.[6] ..... A01H 5/00

[52] U.S. Cl. ..... Plt./76

[58] Field of Search ..... Plt./76, 80

*Primary Examiner*—Howard J. Locker

*Attorney, Agent, or Firm*—Foley & Lardner

[57] ABSTRACT

A new and distinct cultivar of Chrysanthemum plant named 'Empire Nostalgia', characterized by the combined features of soft lavender-pink ray floret color, fully double flowers with no disc florets, capitulum diameter 4.0–4.5 cm, 7.5 week flower response in light/shade programs, compact semi-spreading habit, natural season flowering date of September 25–30, and adaptability to greenhouse or garden cultures.

1 Drawing Sheet

The present invention comprises a new and distinct cultivar of *Dendranthema grandiflora*, referred to by the cultivar name 'Empire Nostalgia'.

'Empire Nostalgia' is a product of a planned breeding program which had the objective of creating new chrysanthemum cultivars with decorative capitulm type, compact spreading habit, early flower response, pleasing flower color, and suitability for production as a garden variety. Such traits in combination were not present in previously available commercial cultivars.

'Empire Nostalgia' was originated from a hybridization made by the inventor in a controlled breeding program in New Hartford, N.Y. in October 1992. The female parent was 'Empire Calypso', disclosed in U.S. Plant Pat. No. 9,584. The male parent of 'Empire Nostalgia' was B89-28, an unnamed seedling identified as a light pink decorative garden mum.

'Empire Nostalgia' was discovered and selected as one flowering plant within the progeny of the stated parentage by Janet S. Fuess in September 1993, in a controlled environmenti in New Hartford, N.Y.

The first act of asexual reproduction of 'Empire Nostalgia' was accomplished when vegetative cuttings were taken from the initial selection in October 1993 in a controlled environment in New Hartford, N.Y., by Janet S. Fuess. Horticultural examination of selected units initiated in September 1994 has demonstrated that the combination of characteristics as herein disclosed for 'Empire Nostalgia' are firmly fixed and are retained through successive generations of asexual reproduction.

'Empire Nostalgia' has not been observed under all possible environmental conditions. The phenotype may vary significantly with variations in environment such as temperature, light intensity and day length, without, however any variation in genotype.

The following observations, measurements and comparisons describe plants grown in New Hartford, N.Y. under natural outdoor conditions which approximate those generally used in commercial practice.

The following traits have been repeatedly observed and are determined to be basic characteristics of 'Empire Nostalgia', which, in combination, distinguish this Chrysanthemum as a new and distinct cultivar:

1. Soft lavender-pink ray floret color.
2. Fully double flowers; no disc florets present.
3. Fully expanded ray florets are each approximately 2.25 cm long and 0.75 cm wide, with tri-dentate tips.

4. Average of 356 ray florets per flower.
5. Capitulum 4.0–4.5 cm in diameter.
6. 7.5 week flower response in light/shade controlled programs.
7. Compact, semi-spreading habit.
8. Natural season flowering date of September 25–30.
9. Adaptability to greenhouse or garden cultures.

Of the many commercial cultivars known to the present inventor, the most similar in comparison to 'Empire Nostalgia' is the female parent 'Empire Calypso'. In comparison to 'Empire Calypso', 'Empire Nostalgia' has a lavender-pink floret color compared to a deep red-purple color of 'Empire Calypso', slightly longer response time in light/shade programs, and a 5–10 day later flower response in natural season. The capitulum size, fully double flowers, and overall height of plant of 'Empire Nostalgia' are similar to those same characteristics of 'Empire Calypso'.

The accompanying color photographic drawing shows typical inflorescence and foliage characteristics of 'Empire Nostalgia', with the colors being as nearly true as possible with illustrations of this type.

In the following description, color references are made to The Royal Horticultural Society (R.H.S.) Colour Chart. The color values were determined between 10:00 a.m. and 1:00 p.m. on Oct. 2, 1996 under 4,000 footcandles of light intensity at New Hartford, N.Y.

Classification:

*Botanical.*—*Dendranthema grandiflora* cv 'Empire Nostalgia'.

*Commercial.*—Formal decorative garden mum.

Inflorencence

Capitulum:

*Form.*—Flat.

*Type.*—Decorative.

*Diameter across face.*—4.0–4.5 cm, when fully expanded.

Corolla of ray florets:

*Color* (*general tonality from a distance of three meters*) .—Lavender-pink.

*Color* (*top surface*).—75B.

*Color* (*under surface*).—75D.

Disc florets: None.

Reproductive organs:

*Androecium.*—None.

*Gynoecium.*—Style 0.5 cm and bifurcated.

Plant

General appearance:

*Height*.—24–28 cm when grown in an 8 inch pot (no growth regulators).

Foliage:

*Color* (*upper surface*).—137A.

*Color* (*under surface*).—137C.

*Shape*.—4.5–6.0 cm long, 3.75–4.25 cm wide, 5-lobed.

I claim:

1. A new and distinct cultivar of chrysanthemum plant named 'Empire Nostalgia', as illustrated and described.

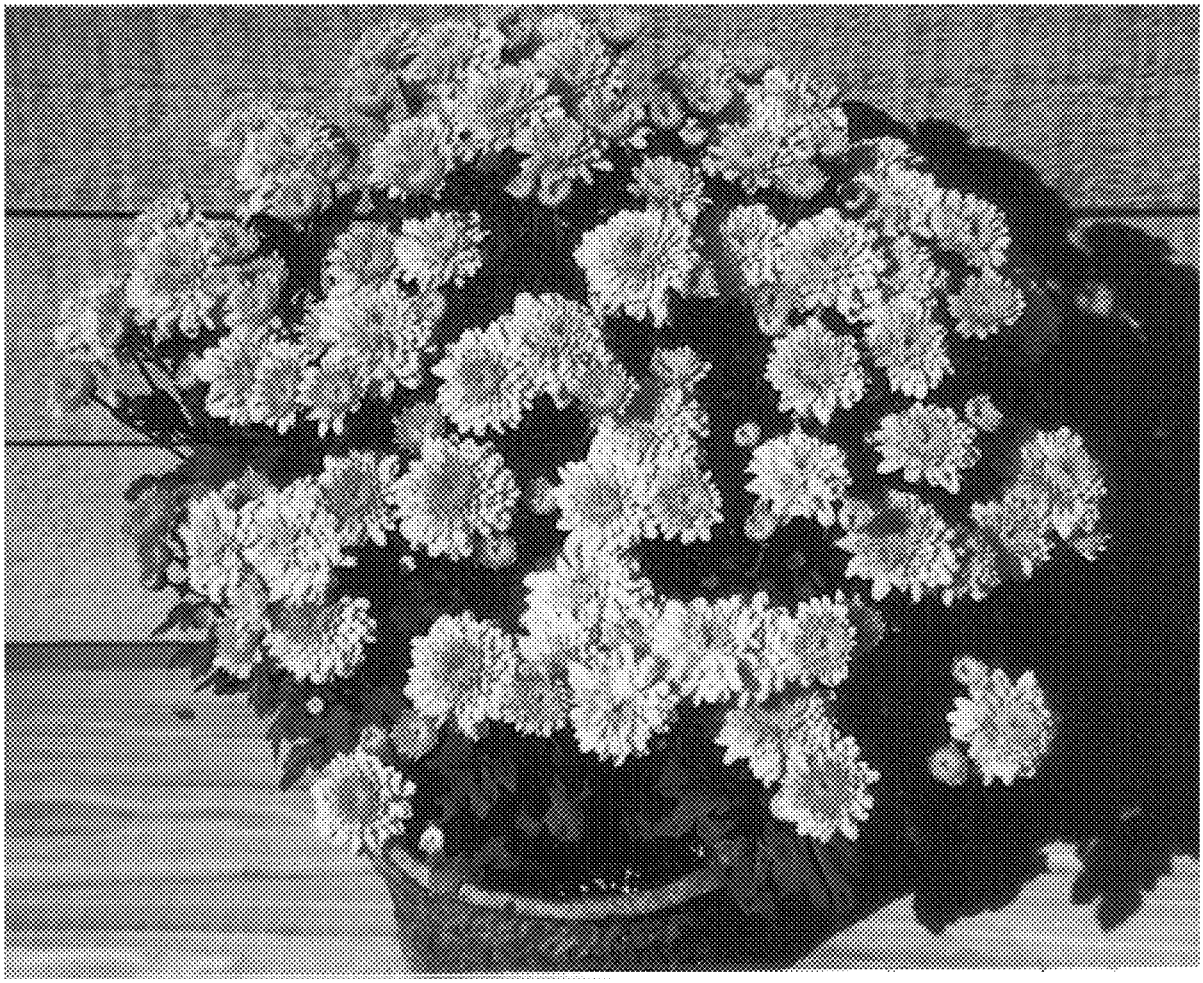

* * * * *